US012599412B2

(12) United States Patent
Glassman et al.

(10) Patent No.: US 12,599,412 B2
(45) Date of Patent: Apr. 14, 2026

(54) INTRA-OPERATIVE OPTIONS FOR SMART IMPLANTS

(71) Applicant: Warsaw Orthopedic, Inc., Warsaw, IN (US)

(72) Inventors: Steven D. Glassman, Louisville, KY (US); Newton H. Metcalf, Jr., Memphis, TN (US); Jerald L. Redmond, Germantown, TN (US); Arjun Siby-Kurian, Memphis, TN (US); Adam D. Glaser, Colliersville, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 116 days.

(21) Appl. No.: 18/542,249

(22) Filed: Dec. 15, 2023

(65) Prior Publication Data

US 2024/0122720 A1     Apr. 18, 2024

Related U.S. Application Data

(63) Continuation-in-part of application No. 18/183,484, filed on Mar. 14, 2023, which is a (Continued)

(51) Int. Cl.
| | |
|---|---|
| *A61B 17/70* | (2006.01) |
| *A61B 5/00* | (2006.01) |
| *A61B 90/00* | (2016.01) |

(52) U.S. Cl.
CPC ........ *A61B 17/7002* (2013.01); *A61B 5/0022* (2013.01); *A61B 5/4566* (2013.01); (Continued)

(58) Field of Classification Search
CPC ....................... A61B 17/7001–17/7031; A61B 17/7041–17/7046;
(Continued)

(56) References Cited

U.S. PATENT DOCUMENTS

| | | |
|---|---|---|
| 3,444,775 A | 5/1969 | Hills |
| 5,697,929 A | 12/1997 | Mellinger |

(Continued)

FOREIGN PATENT DOCUMENTS

| | | |
|---|---|---|
| JP | 2015532841 A | 11/2015 |
| KR | 10-1851690 B1 | 4/2018 |

(Continued)

OTHER PUBLICATIONS

International Search Report, PCT/US2019/042511, Oct. 31, 2019.
(Continued)

*Primary Examiner* — Julianna N Harvey
(74) *Attorney, Agent, or Firm* — FOX ROTHSCHILD LLP

(57) ABSTRACT

A method of treating a spine includes implanting at least a portion of a spinal construct in a patient. The method further includes attaching one or more smart implants to the spinal construct. Each of the one or more smart implants includes (a) an attachment portion configured to attach the smart implant to the spinal construct, and (b) at least one sensor configured to measure an aspect of the spinal construct when the smart implant is attached to the spinal construct. The method further includes receiving, from the one or more smart implants, sensor information related to the aspect of the spinal construct and performing at least one intra-operational adjustment to the spinal construct based on the received sensor information.

21 Claims, 5 Drawing Sheets

Related U.S. Application Data continuation-in-part of application No. 18/068,140, filed on Dec. 19, 2022, and a continuation-in-part of application No. 18/062,867, filed on Dec. 7, 2022, now Pat. No. 12,465,408.

(60) Provisional application No. 63/329,982, filed on Apr. 12, 2022.

(52) U.S. Cl.
CPC .............. *A61B 5/686* (2013.01); *A61B 5/742* (2013.01); *A61B 17/7032* (2013.01); *A61B 2090/064* (2016.02)

(58) Field of Classification Search
CPC . A61B 17/7032–17/704; A61B 5/0031; A61B 5/0024; A61B 5/4566; A61B 5/4851; A61B 5/686; A61B 2562/0261; A61B 17/7049–17/7052
See application file for complete search history.

(56) References Cited

U.S. PATENT DOCUMENTS

| | | | |
|---|---|---|---|
| 6,004,349 A | 12/1999 | Jackson | |
| 6,179,841 B1 | 1/2001 | Jackson | |
| 6,280,445 B1 | 8/2001 | Morrison et al. | |
| 6,485,491 B1 | 11/2002 | Farris et al. | |
| 6,884,244 B1 | 4/2005 | Jackson | |
| 7,357,037 B2 | 4/2008 | Hnat et al. | |
| 7,993,269 B2 | 8/2011 | Donofrio et al. | |
| 8,057,519 B2 | 11/2011 | Justis et al. | |
| 8,372,147 B2 | 2/2013 | Roche | |
| 8,868,200 B2 | 10/2014 | Abrahamson et al. | |
| 8,882,803 B2 * | 11/2014 | Lott | A61B 17/7002 606/264 |
| 9,241,738 B2 | 1/2016 | Quevedo et al. | |
| 9,498,294 B2 | 11/2016 | Rigsby et al. | |
| 9,585,602 B1 | 3/2017 | Navarro et al. | |
| 9,711,840 B2 | 7/2017 | Lin | |
| 10,219,699 B2 | 3/2019 | Wilder et al. | |
| 10,362,982 B2 | 7/2019 | Stevenson et al. | |
| 2003/0073996 A1 * | 4/2003 | Doubler | A61B 17/7041 606/301 |
| 2005/0018749 A1 | 1/2005 | Sato et al. | |
| 2005/0187549 A1 | 8/2005 | Jackson | |
| 2005/0228326 A1 | 10/2005 | Kalfas et al. | |
| 2005/0267477 A1 | 12/2005 | Jackson | |
| 2006/0052782 A1 | 3/2006 | Morgan et al. | |
| 2007/0017295 A1 | 1/2007 | Ohta et al. | |
| 2007/0073300 A1 | 3/2007 | Attawia et al. | |
| 2007/0100218 A1 | 5/2007 | Sweitzer et al. | |
| 2008/0133009 A1 | 6/2008 | Caylor | |
| 2008/0281212 A1 | 11/2008 | Nunez et al. | |
| 2009/0143696 A1 | 6/2009 | Najafi et al. | |
| 2009/0171178 A1 | 7/2009 | He et al. | |
| 2009/0198273 A1 * | 8/2009 | Zhang | A61B 17/8685 606/264 |
| 2009/0228074 A1 | 9/2009 | Edgell et al. | |
| 2009/0234391 A1 | 9/2009 | Butler et al. | |
| 2009/0298650 A1 | 12/2009 | Kutliroff | |
| 2010/0152621 A1 | 6/2010 | Janna et al. | |
| 2010/0201118 A1 | 8/2010 | Anton et al. | |
| 2010/0217331 A1 | 8/2010 | Spagnoli et al. | |
| 2010/0298886 A1 | 11/2010 | Kraus et al. | |
| 2011/0106179 A1 | 5/2011 | Prevost et al. | |
| 2011/0213221 A1 | 9/2011 | Roche | |
| 2011/0319755 A1 | 12/2011 | Stein et al. | |
| 2012/0059389 A1 | 3/2012 | Larson et al. | |
| 2012/0143029 A1 | 6/2012 | Silverstein et al. | |
| 2012/0221057 A1 * | 8/2012 | Zhang | A61B 17/7086 606/279 |
| 2013/0072982 A1 | 3/2013 | Simonson | |
| 2013/0076157 A1 | 3/2013 | Stein | |
| 2013/0079669 A1 | 3/2013 | Stein et al. | |
| 2013/0079680 A1 | 3/2013 | Stein et al. | |
| 2013/0096396 A1 | 4/2013 | Riedel | |
| 2013/0253334 A1 | 9/2013 | Al-Ali et al. | |
| 2014/0214097 A1 | 7/2014 | Jackson et al. | |
| 2015/0080901 A1 | 3/2015 | Stein | |
| 2015/0164401 A1 | 6/2015 | Toth et al. | |
| 2015/0201974 A1 | 7/2015 | DeRidder et al. | |
| 2015/0257687 A1 | 9/2015 | Pushpala et al. | |
| 2016/0128573 A1 | 5/2016 | Wilder et al. | |
| 2016/0235480 A1 * | 8/2016 | Scholl | A61B 34/10 |
| 2016/0331415 A1 | 11/2016 | Serhan et al. | |
| 2017/0007420 A1 | 1/2017 | Stevenson et al. | |
| 2017/0079555 A1 | 3/2017 | Munro et al. | |
| 2017/0138387 A1 | 5/2017 | Saigo et al. | |
| 2017/0196499 A1 | 7/2017 | Hunter | |
| 2017/0196508 A1 * | 7/2017 | Hunter | A61B 5/4566 |
| 2017/0231559 A1 | 8/2017 | Cuevas et al. | |
| 2018/0195547 A1 | 7/2018 | Demeocq | |
| 2018/0310964 A1 | 11/2018 | Stevenson et al. | |
| 2019/0038214 A1 | 2/2019 | Mikhail et al. | |
| 2019/0344070 A1 | 11/2019 | Molnar et al. | |
| 2019/0346313 A1 | 11/2019 | Cox | |
| 2020/0022733 A1 | 1/2020 | Benson et al. | |
| 2020/0022735 A1 | 1/2020 | Fields et al. | |
| 2020/0022739 A1 | 1/2020 | Benson et al. | |
| 2020/0022740 A1 | 1/2020 | Benson et al. | |
| 2020/0022772 A1 | 1/2020 | Benson et al. | |
| 2020/0069247 A1 | 3/2020 | Hunter | |
| 2020/0085366 A1 | 3/2020 | Benson et al. | |
| 2020/0297513 A1 | 9/2020 | Zellmer et al. | |
| 2020/0330230 A1 | 10/2020 | Macewan et al. | |
| 2020/0405239 A1 | 12/2020 | Trabish et al. | |
| 2021/0153909 A1 | 5/2021 | Siby-Kurian et al. | |
| 2021/0186567 A1 | 6/2021 | Bobbitt et al. | |
| 2021/0361377 A1 | 11/2021 | Metcalf et al. | |
| 2022/0160428 A1 * | 5/2022 | Murray | A61B 17/7086 |
| 2022/0273391 A1 | 9/2022 | Metcalf, Jr. et al. | |
| 2022/0378370 A1 | 12/2022 | Pasha | |

FOREIGN PATENT DOCUMENTS

| | | |
|---|---|---|
| WO | 2013109762 A1 | 7/2013 |
| WO | 2015200720 A2 | 12/2015 |
| WO | 2017006068 A1 | 1/2017 |
| WO | 2017007821 A1 | 1/2017 |
| WO | 2017165717 A1 | 9/2017 |
| WO | 2017180653 A1 | 10/2017 |
| WO | 2020018862 A1 | 1/2020 |

OTHER PUBLICATIONS

International Search Report, PCT/US2019/042516, Oct. 31, 2019.
International Search Report and Written Opinion, PCT/US2020/041487 mailed Nov. 2, 2020.
European Search Report in Application No. 21168012.9 dated Sep. 20, 2021.
International Search Report and Written Opinion in Application No. PCT/US2019/050717 mailed Jan. 3, 2020.
Rodriguez-Martin, et al. "A wearable inertial measurement unit for long-term monitoring in the dependency care area." Sensors 13.10 (2013): 14079-14104. (Year: 2016).
Conway, Justin, Christy C. Tomkins, and Andrew J. Haig. "Walking assessment in people with lumbar spinal stenosis: capacity, performance, and self-report measures." The Spine Journal 11.9 (2011): 816-823. (Year: 2011).
Trost, et al. "Conducting accelerometer-based activity assessments in field-based research." Medicine & Science in Sports & Exercise 37.11 (2005): S531-S543. (Year: 2005).
Liu, Ye, et al. "From action to activity: sensor-based activity recognition." Neurocomputing 181 (2016): 108-115. (Year: 2016).
Ahmadi, Amin, et al. "Automatic activity classification and movement assessment during a sports training session using wearable inertial sensors." 2014 11th International Conference on Wearable and Implantable Body Sensor Networks. IEEE, 2014. (Year: 2014).

(56)             References Cited

OTHER PUBLICATIONS

International Search Report for corresponding application No. PCT/US2019/050717 dated Sep. 12, 2019.

European Search Report in Appln. No. 21168012.9 dated Sep. 20, 2021.

European Search Report in Application No. 19838132.9 dated Apr. 4, 2022.

European Search Report in Application No. 19837036.3 dated Apr. 4, 2022.

European Search Report in Application No. 19838911.6 dated Apr. 4, 2022.

International Search Report for corresponding application No. PCT/US2019/050717 with Intl Filing date Sep. 12, 2019.

European Search Report in Application No. 20837889 dated Apr. 25, 2023.

Karipott Salil Sidharthan et al: "An Embedded Wireless Temperature Sensor for Orthopedic Implants", IEEE Sensors Journal, IEEE, USA, vol. 18, No. 3, Feb. 1, 2018 (Feb. 1, 2018), pp. 1265-1272, XP011675608, ISSN: 1530-437X, DOI: 10.1109/JSEN.2017.2780226.

International Search Report and Written Opinion in Application No. PCT/IB2023/053705 dated Jul. 7, 2023.

International Search Report and Written Opinion in Application No. PCT/IB2023/053707 dated Jul. 24, 2023.

Chinese Office Action in Application No. 201980047442.2 dated Jun. 27, 2023.

International Search Report and Written Opinion in Application No. PCT/IB2023/053713 dated Jul. 28, 2023.

International Search Report in Application No. PCT/IB2024/054039 date of completion is Jun. 27, 2024 (13 pages).

* cited by examiner

INTRA-OPERATIVE OPTIONS FOR SMART IMPLANTS

CROSS-REFERENCE TO RELATED APPLICATIONS

This application is a continuation-in-part of U.S. application Ser. No. 18/183,484, titled SPINAL IMPLANTS WITH ELECTRONICS CARTRIDGE AND EXTERNAL-IZED ANTENNA, filed Mar. 14, 2023, which claims priority to U.S. Provisional Application 63/329,982, titled SMART IMPLANT DESIGNS FOR HOUSING A POWER SOURCE, ANTENNA, GAUGES, AND MICROELEC-TRONICS, and filed Apr. 12, 2022. U.S. application Ser. No. 18/183,484 is also a continuation-in-part of U.S. application Ser. No. 18/062,867, titled SPINAL ROD CONNECTING COMPONENTS WITH ACTIVE SENSING CAPABILI-TIES, filed Dec. 7, 2022 and U.S. application Ser. No. 18/068,140, titled SPINAL IMPLANTS WITH ACTIVE SENSING CAPABILITIES, filed Dec. 19, 2022. The disclosures of these applications are incorporated herein by reference in their entirety.

FIELD

The present disclosure generally relates to mechanical and electrical sensor assemblies and antenna designs for implant devices, and more particularly to intra-operative application of sensor assemblies.

BACKGROUND

Treatment of spinal disorders, such as degenerative disc disease, disc herniations, scoliosis or other curvature abnormalities, and fractures, often requires surgical treatments. For example, spinal fusion may be used to limit motion between vertebral members. As another example, implants may be used to preserve motion between vertebral members.

Surgical treatment typically involves the use of implants and longitudinal members, such as spinal rods. Implants may be disposed between two vertebral members for supporting and/or repositioning the vertebral members. Implants may also be used to facilitate a fusion process between a superior vertebra and an inferior vertebra. Longitudinal members may be attached to the exterior of two or more vertebral members to assist with the treatment of a spinal disorder. Longitudinal members may provide a stable, rigid column that helps bones to fuse, and may redirect stresses over a wider area away from a damaged or defective region. Also, rigid longitudinal members may help in spinal alignment.

Screw assemblies may be used to connect a longitudinal member to a vertebral member. A screw assembly may include a pedicle screw, hook, tulip bulb connector or other type of receiver, and a set screw, among other components. A pedicle screw can be placed in, above and/or below vertebral members that were fused, and a longitudinal member can be used to connect the pedicle screws which inhibit or control movement. A set screw can be used to secure the connection of a longitudinal member and a pedicle screw, hook, or other connector. Implants may include one or more sensors for monitoring post-operative aspects of the treatment and transmitting sensor data to an external reader. However, it would be advantageous to apply sensor assemblies intra-operatively, to facilitate attaching and configuring implants for improved outcomes without waiting for post-operative monitoring to indicate issues.

SUMMARY

The techniques of this disclosure generally relate to intraoperative application of sensor assemblies having various sensors for communicating, to an external reader, attributes about spinal implants being attached and/or configured. In an example embodiment a method of treating a spine is disclosed. The method includes implanting at least a portion of a spinal construct in a patient. The method further includes attaching one or more smart implants to the spinal construct. Each of the one or more smart implants includes (a) an attachment portion configured to attach the smart implant to the spinal construct, and (b) at least one sensor configured to measure an aspect of the spinal construct when the smart implant is attached to the spinal construct. The method further includes receiving, from the one or more smart implants, sensor information related to the aspect of the spinal construct and performing at least one intra-operational adjustment to the spinal construct based on the received sensor information.

Implementations of the disclosure may include one or more of the following optional features. In some examples, performing the at least one intra-operational adjustment to the spinal construct includes (a) bending a spinal rod of the spinal construct, (b) adding a cross link to the spinal construct, or (c) affixing the spinal construct to the patient at one or more additional points. The method may further include removing the one or more smart implants after performing the at least one intra-operational adjustment to the spinal construct. The one or more smart implants may include multiple smart implants. In some examples, at least one smart implant includes a force sensor and receiving the sensor information related to the aspect of the spinal construct includes receiving information from the force sensor. Receiving the information from the force sensor may include receiving strain data from the force sensor. In some examples, at least one smart implant includes a position sensor and receiving the sensor information related to the aspect of the spinal construct includes receiving information related to a position of the smart implant when the smart implant is attached to the spinal construct. In some examples, at least one smart implant includes an antenna and receiving the sensor information related to the aspect of the spinal construct includes receiving the sensor information wirelessly. Performing the at least one intra-operational adjustment to the spinal construct may include implanting additional construct components.

Attaching the one or more smart implants to the spinal construct may include adding a provisional component to the spinal construct and attaching at least one of the one or more smart implants to the provisional component. In some examples, the method further includes attaching the at least one of the one or more smart implants to a part of the patient's anatomy. The method may further include, after performing the at least one intra-operational adjustment to the spinal construct, removing the provisional component. In some examples, the spinal construct includes a spinal rod and attaching the one or more smart implants to the spinal construct includes securing the spinal rod within an opening of at least one of the one or more smart implants. Performing the at least one intra-operational adjustment to the spinal construct may include redistributing forces among vertebrae of the patient. The method may further include attaching at least one of the one or more smart implants to a part of the patient's anatomy. In some examples, the at least one of the one or more smart implants includes a bone screw and attaching the at least one of the one or more smart implants to the part of the patient's anatomy includes attaching the at least one of the one or more smart implants to a bone using the bone screw. The method may further include, after performing the at least one intra-operational adjustment to the spinal construct, detaching the at least one of the one or more smart implants from the part of the patient's anatomy. In some examples, receiving the sensor information related to the aspect of the spinal construct includes receiving the sensor information by a reader device. Receiving the sensor information related to the aspect of the spinal construct may include viewing a plot of the sensor information displayed by the reader device. Receiving the sensor information related to the aspect of the spinal construct may include receiving a notification from the reader device that one or more of the sensor measurements are outside of a value range.

DETAILED DESCRIPTION

Figure 1:
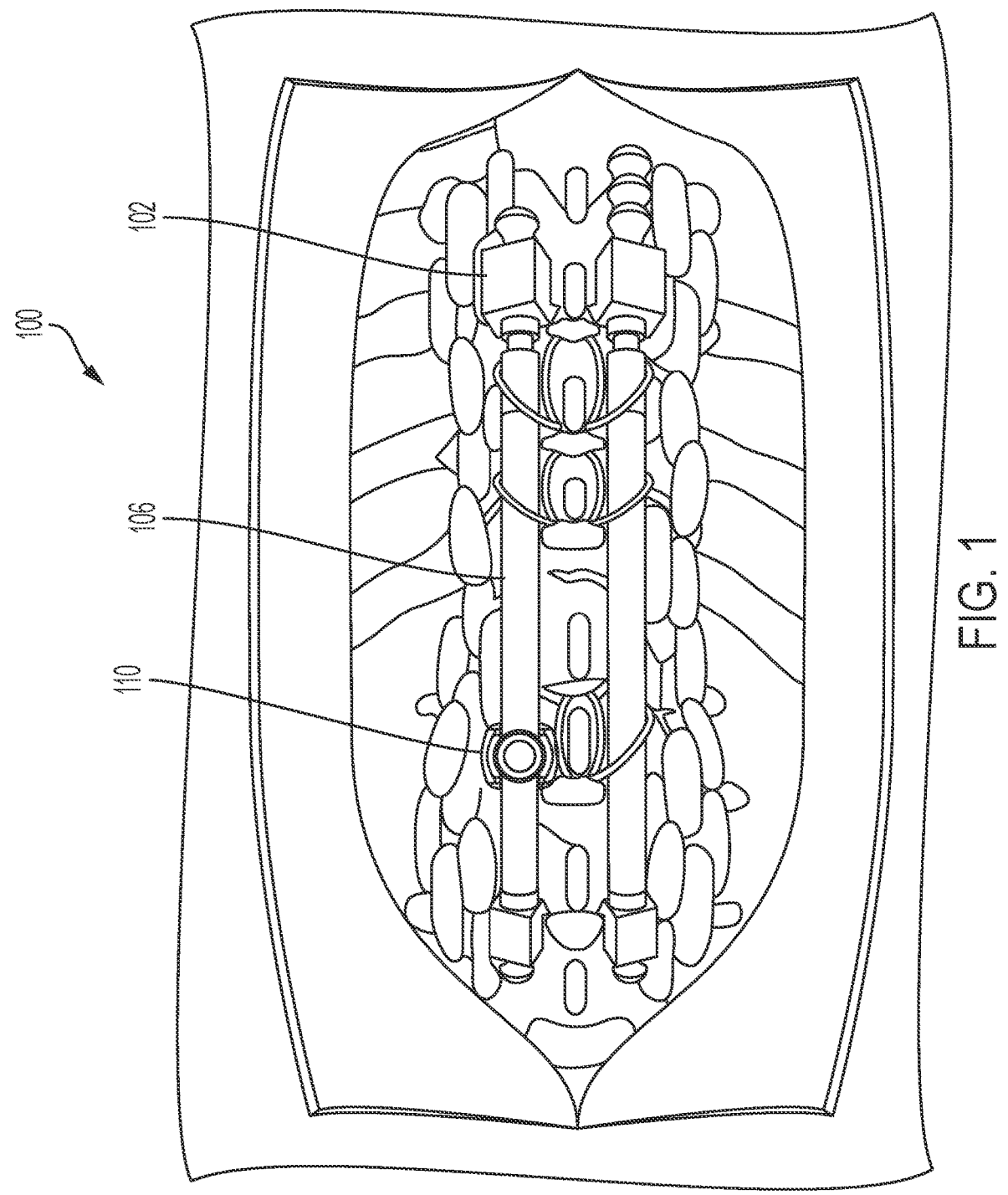
FIG. 1 shows an example environment 100 for performing a surgical procedure.

Embodiments of the present disclosure relate generally, for example, to intraoperative application of spinal implants having sensor assemblies. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise. The term "about" may encompass a meaning of being +/−10% of the stated value.

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

Referring to the disclosed embodiments generally, components of the implant systems can be fabricated from biologically acceptable materials suitable for medical applications, including metals, synthetic polymers, ceramics and bone material and/or their composites. The components may be fabricated using bio-inert materials, such as metals, ceramics, polymers, etc. The components may also be fabricated (either entirely or at least partially) using bio-resorbable or bio-convertible materials, as appropriate. For example, the components, individually or collectively, can be fabricated from materials such as stainless steel alloys, commercially pure titanium, titanium alloys, Grade 5 titanium, super-elastic titanium alloys, cobalt-chrome alloys, super-elastic metallic alloys (e.g., Nitinol, super-elastoplastic metals, such as GUM METAL®), ceramics and composites thereof such as calcium phosphate (e.g., SKELITE™), alumina, yttria-stabilized zirconia (YSZ), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyketide, polyglycolide, polytyrosine carbonate, polycaprolactone, polylactic acid or polylactide and their combinations.

Various components of the implant system may be formed or constructed with material composites, including the above materials, to achieve various desired characteristics such as strength, rigidity, elasticity, compliance, biomechanical performance, durability and radiolucency or imaging preference. The components of the present implant system, individually or collectively, may also be fabricated from a heterogeneous material such as a combination of two or more of the above-described materials. The components of the implant system may be monolithically formed, integrally connected or include fastening elements and/or instruments, as described herein. The components of the implant system may be formed using a variety of subtractive and additive manufacturing techniques, including, but not limited to machining, milling, extruding, molding, 3D-printing, sintering, coating, vapor deposition, and laser/beam melting.

Furthermore, various components of the implant system may be coated or treated with a variety of additives or coatings to improve biocompatibility, bone growth promotion or other features. Various embodiments and components may be coated with a ceramic, titanium, and/or other biocompatible material to provide surface texturing at (a) the macro scale, (b) the micro scale, and/or (c) the nano scale, for example. Similarly, components may undergo a subtractive manufacturing process such as, for example, grit blasting and acid etching, providing for surface texturing configured to facilitate osseointegration and cellular attachment and osteoblast maturation. Example surface texturing of additive and subtractive manufacturing processes may include (a) macro-scale structural features having a maximum peak-to-valley height of about 40 microns to about 500 microns, (b) micro-scale structural features having a maximum peak-to-valley height of about 2 microns to about 40 microns, and/or (c) nano-scale structural features having a maximum peak-to-valley height of about 0.05 microns to about 5 microns. In various embodiments, the three types of structural features may be overlapping with one another. Additionally, such surface texturing may be applied to any surface, e.g., both external exposed facing surfaces of components and internal non exposed surfaces of components. Further discussion regarding relevant surface texturing and coatings is described in, for example, U.S. Pat. No. 11,096, 796, titled Interbody spinal implant having a roughened surface topography on one or more internal surfaces, and filed on Mar. 4, 2013—the entire disclosure of which is incorporated herein by reference in its entirety. Accordingly, it shall be understood that any of the described coating and texturing processes of U.S. Pat. No. 11,096,796, may be applied to any component of the various embodiments disclosed herein, e.g., the exposed surfaces and internal surfaces. Another example technique for manufacturing an orthopedic implant having surfaces with osteoinducting roughness features including micro-scale structures and nano-scale structures is disclosed in U.S. Pat. No. 10,821, 000, the entire contents of which are incorporated herein by reference. Additionally, an example of a commercially available product may be the Adaptix™ Interbody System sold by Medtronic Spine and comprising a titanium cage made with Titan nanoLOCK™.

The disclosed implant systems may be employed, for example, during a minimally invasive procedure, including percutaneous techniques, mini-open and open surgical techniques to deliver and introduce instrumentation and/or one or more spinal implants at a surgical site within a body of a patient, for example, a section of a spine. In some embodiments, the implant system may be employed during surgical procedures, as described herein, and/or, for example, corpectomy, discectomy, fusion and/or fixation treatments that employ spinal implants to restore the mechanical support function of vertebrae. In some embodiments, the implant system may be employed during surgical approaches, including but not limited to: anterior lumbar interbody fusion (ALIF), direct lateral interbody fusion (DLIF), oblique lateral lumbar interbody fusion (OLLIF), oblique lateral interbody fusion (OLIF), transforaminal lumbar Interbody fusion (TLIF), posterior lumbar Interbody fusion (PLIF), various types of posterior or anterior fusion procedures, and any fusion procedure in any portion of the spinal column (sacral, lumbar, thoracic, and cervical).

The disclosed smart implant embodiments include sensor assemblies that are configured to provide telemetry to an external device during the procedure. That is, the sensor assemblies are configured to sense and/or acquire data related to aspects of the surgical procedure, such as forces between spinal implants or components, e.g., during attachment and/or configuration of a spinal construct. The sensor assemblies may also sense aspects and/or acquire data related to the surgical site, such as temperature readings from a variety of locations around the surgical site or data related to position and/or motion of the patient's spine during surgery. The sensor assemblies may be further configured to store and/or transmit the sensed/acquired data in the form of telemetry to a remote monitoring system. Telemetry data may include position/motion information, force/strain information, temperature, tissue impedance, and so forth. For example, the spinal implants may be installed during a surgical procedure such as a spinal fusion. The spinal implants may also provide telemetry related to the surgical site, such as temperature readings from a variety of locations around the surgical site or telemetry related to position and/or motion of the patient's spine during surgery. In these cases and others, an external reader, such as the system disclosed in U.S. patent application Ser. No. 16/855, 444, incorporated herein by reference in its entirety, may receive and display or otherwise provide the telemetry intra-operatively to a medical professional for evaluation. In some examples, the reader is configured to be disposed at or near a patient's bedside, allowing the patient and the medical professional to readily observe the displayed status information. The external reader may also receive telemetry from other sources such as, but not limited to, one or more wearable sensor systems that are affixed to the patient. The reader device itself may include additional sensors as well.

The smart implants may include electronics, such as sensors or sensor assemblies which acquire the data, and transmitter (or transceiver) systems which transmit the acquired data as telemetry to the external reader/receiver device. The smart implants may also include a power source, such as a battery (rechargeable or otherwise) for powering the electronics. The transmitter system may include an antenna for radiating the telemetry signal to the reader device (and/or an intermediate relay device).

In some examples, the smart implants are configured for use in physically confined areas, such as the space between a spinal construct being attached to the patient's spine and a part of the patient's anatomy, e.g., the patient's spine. As such, the smart implants may be designed to be physically compact, e.g., to take up as little space as reasonably possible while providing telemetry. In some examples, the smart implants are configured to provide telemetry only during the procedure, which may last several hours. Thus, the smart implants may be advantageously configured to include a relatively small power source to help achieve a compact configuration.

Furthermore, the tissue surrounding the implant may constrain antenna configuration. For example, a rigid antenna extending away from a spinal implant may irritate or damage surrounding tissue. The level of irritation or damage may be related to the type of tissue as well as the construction and/or configuration of the antenna. Thus, the smart implants may be advantageously configured to include antennae designed to avoid irritating or damaging tissue during the procedure. In some examples, the smart implants include internal antenna to avoid irritating or damaging tissue.

FIG. 1 shows an example environment 100 for performing a surgical procedure such as a spinal fusion. The procedure may include attaching rigid (or semi-rigid) metallic or non-metallic devices to the patient's spine to form a spinal construct 102. The spinal construct 102 may include components such as pedicle screws, iliac screws or other bone screws, transverse process hooks, rods, cross connectors, accessories, and so forth. In general, spinal constructs 102 provide spinal stability/support, limit undesirable movement, redistribute forces among vertebrae, and/or apply corrective forces to vertebrae. Construct design requires understanding of the condition being treated and the biomechanical forces acting on the spine (and on the installed construct 102). Creating a preoperative plan, or blueprint, can focus this design process. The preoperative plan may be based on information obtained from clinical assessment, imaging studies, and so forth. However, flexibility may be required during the procedure because of unexpected findings. An improperly installed or configured construct 102 may result in poor clinical outcomes, including proximal junctional kyphosis (PJK). Thus, access to additional intraoperational information related to forces applied by (or experienced by) spinal construct components may be advantageously used to achieve improved outcomes and reduce the need for revision surgery.

As shown in FIG. 1, the construct 102 may include one or more smart implants 110, which may be temporarily attached to rod 106 during the procedure, and which provide telemetry to an external reader device (not shown). As described above, some or all of the smart implants 110 may be designed to be physically compact, such that they can be located in confined spaces. The smart implants 110 may sense motion, position, or temperature of the spinal construct 102 and provide the sensed information as telemetry. Additional smart implants 110 may be added to the construct 102 as the construct 102 is assembled and attached to the patient's spine, e.g., at additional points, during the procedure. The construct may be attached to the spine using hooks, screws, tethers, and so forth.

Figure 2:
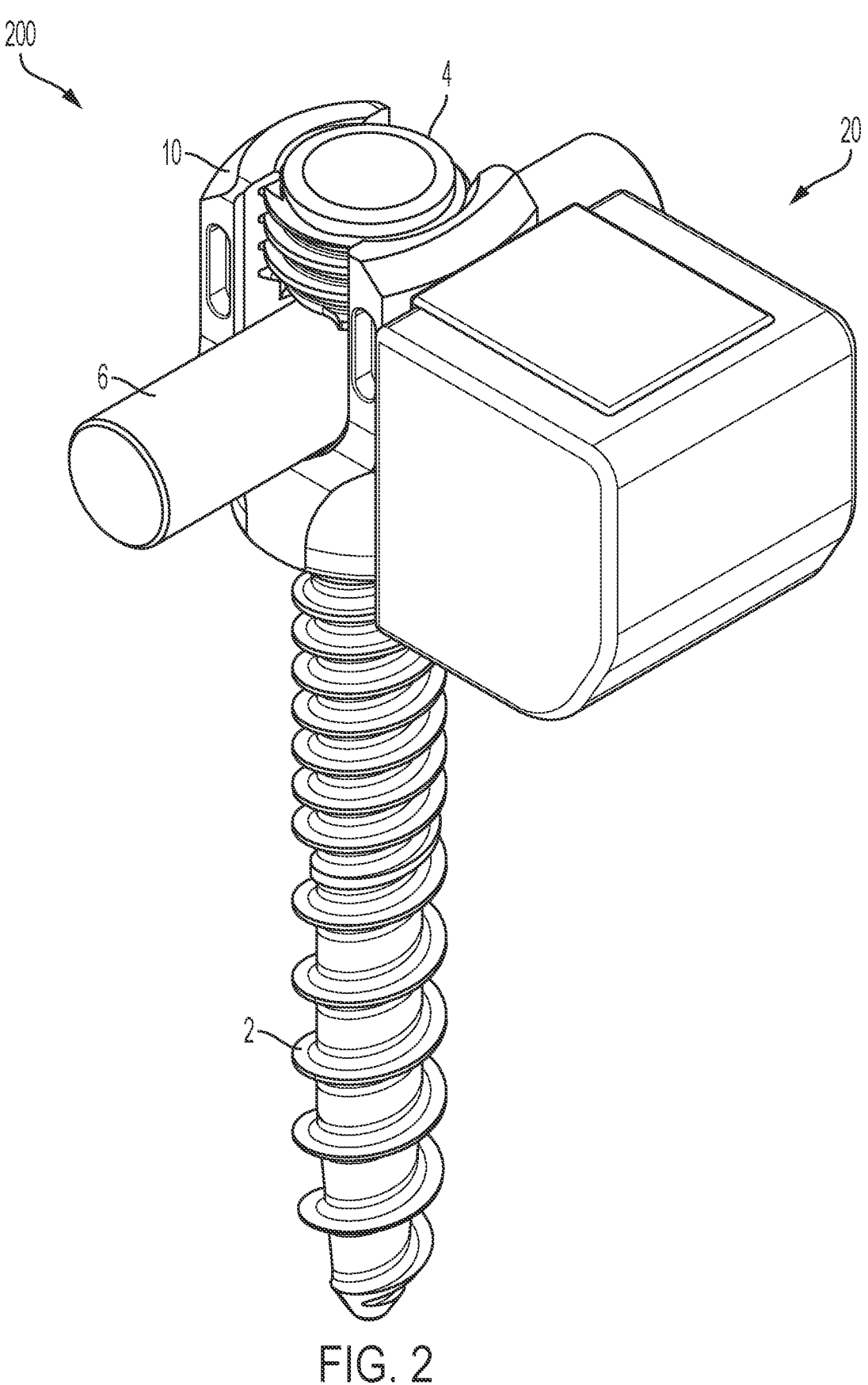
FIG. 2 illustrates an example smart implant.

FIG. 2 illustrates an example digital pedicle screw system 200 with active sensing ability. The system 200 may include a pedicle screw 2 and a receiver 10 having a side portion 20 for supporting various electronic components and sensors as will be explained in further detail below. The pedicle screw 2 may have a thread pitch extending along a length thereof for implanting and securing the pedicle screw 2 into patient anatomy, e.g., a vertebral body. The pedicle screw 2 may include a head portion (not shown) that may couple to the receiver 10 in a lower cavity (not shown). In various embodiments, a lower cavity of receiver 10 may include at least one annular groove for supporting a deformable annular ring or c-ring that captures the head of pedicle screw 2. In this way, receiver 10 may be popped on to the head of a pedicle screw 2 simply by pressing down on receiver 10 as would be understood by a person of ordinary skill in the art. In some examples, this locking mechanism may be omitted so that the pedicle screw 2 may be easily de-coupled from the lower cavity.

In various embodiments, the lower cavity and head may be configured to enable coupling of receiver 10 in a multitude of angled orientations with respect to the extension direction of pedicle screw 2. For example, receiver 10 may be configured as a multiaxial receiver. In other embodiments, receiver 10 may be configured as a monoaxial receiver. In various embodiments a saddle may be disposed within the lower cavity of receiver 10 to support a longitudinal rod 6 disposed in the U-shaped cavity of receiver 10. A set screw 4 may engage to threads of each respective arm of the U-shaped cavity of receiver 10. When sufficiently tightened, set screw 4 may immobilize and/or secure the longitudinal rod 6 within the U-shaped cavity of receiver 10. Other configurations for securing the longitudinal rod 6 or otherwise attaching the smart implant 110 to the construct are also within the scope of this disclosure.

Receiver 10 may be coupled to side portion 20, e.g., via a beam portion. In various embodiments, receiver 10 and side portion 20 may be monolithically formed as a single piece or receiver 10 and side portion 20 may be separable pieces that are connected together. In the example embodiment, receiver 10 and side portion 20 are monolithically formed and/or integrally formed together. For example, the receiver 10 is integrally formed with the side portion 20 and they are connected via the beam portion. This arrangement may have the advantage of facilitating the transfer of stress and strain between the receiver 10 and side portion 20 as will be explained in further detail below.

Figure 3:
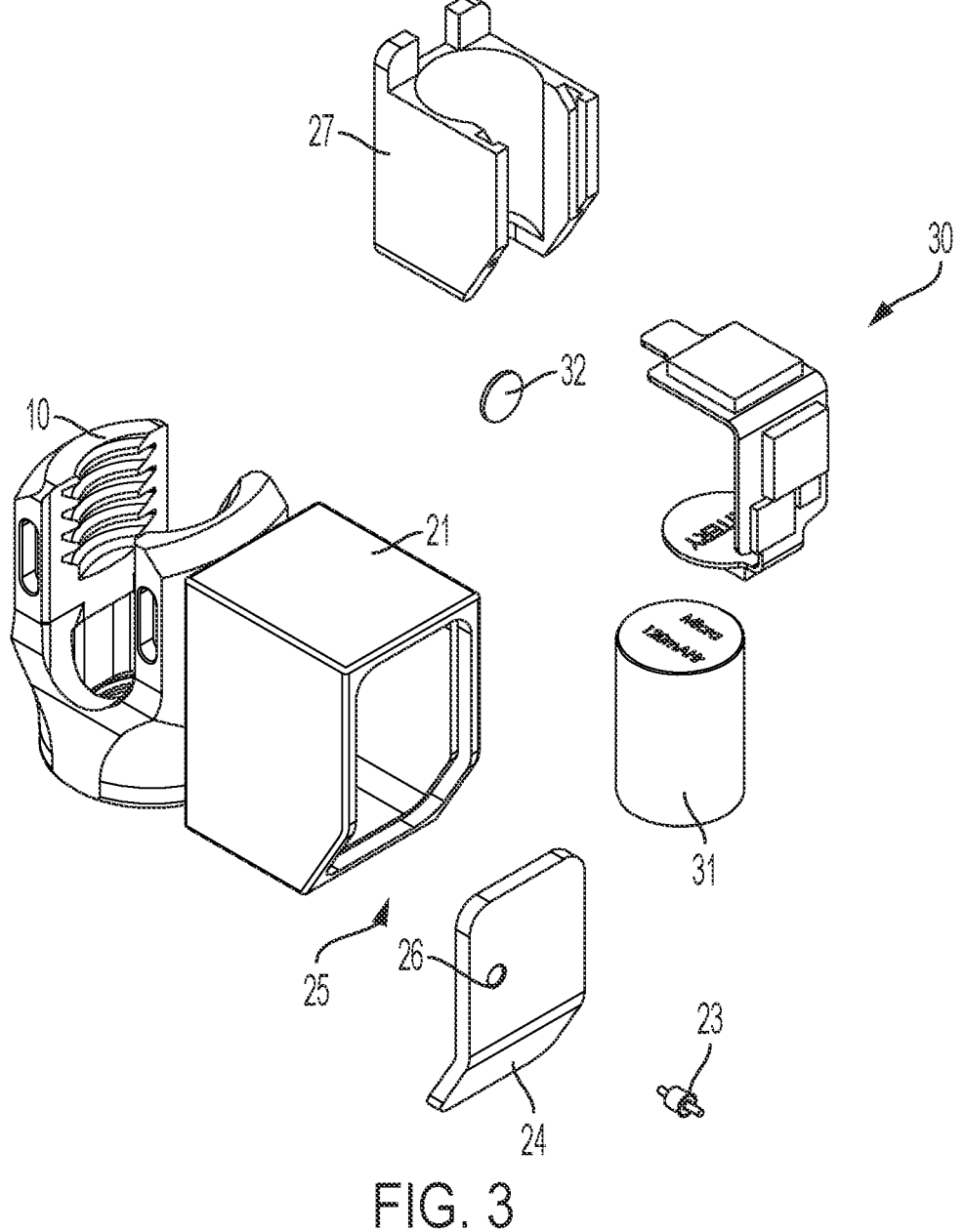
FIG. 3 shows an exploded view of an example smart implant.

FIG. 3 shows an exploded view of an example compact smart implant 110. Housing 21 may define a cavity 25 therein for supporting various electronic components assembled in a microelectronics assembly 30 and a battery 31. In various embodiments, cavity 25 of housing 21 may be hermetically sealed such that the microelectronics assembly 30 and battery therein will not harm a patient when the smart implant 110 is installed within the human body. The battery 31 and microelectronics assembly 30 may be installed within the cavity 25 in any suitable way. In the example embodiment, frame 27 may support the battery 31 and microelectronics assembly 30 securely within the cavity such that the microelectronics, battery 31, sensor 32 (e.g., strain gauge, temperature sensor), and antenna portion 22 are electrically connected. Due to the hermetically sealed nature of cavity 25, a feed-through connection 23 having suitable waterproof flanges may extend through an aperture 26 of cover 24. In this way, the feed-through connection 23 may be electrically connected to the microelectronics assembly 30 and an external antenna portion 22 (not shown) while ensuring that a hermetic seal of the electronics components is possible.

The external antenna portion 22 may include a monopole or "whip" antenna made of a flexible material and is configured to be free floating. That is, the antenna may extend away from the smart implant 110 and into the surrounding tissue and be free to move with respect to the surrounding tissue. The tissue surrounding the smart implant, consisting primarily of muscle tissue, may tolerate a flexible antenna more than more sensitive tissue (e.g., nerves and/or blood vessels). The antenna may also extend toward the patient's skin, i.e., closer to an external reader. By extending closer to an external reader, the transmitted signal will have less tissue to pass through to reach the reader and, therefore, the signal will be less attenuated than a similar signal transmitted from a corresponding internal antenna of the smart implant 110.

Figure 4:
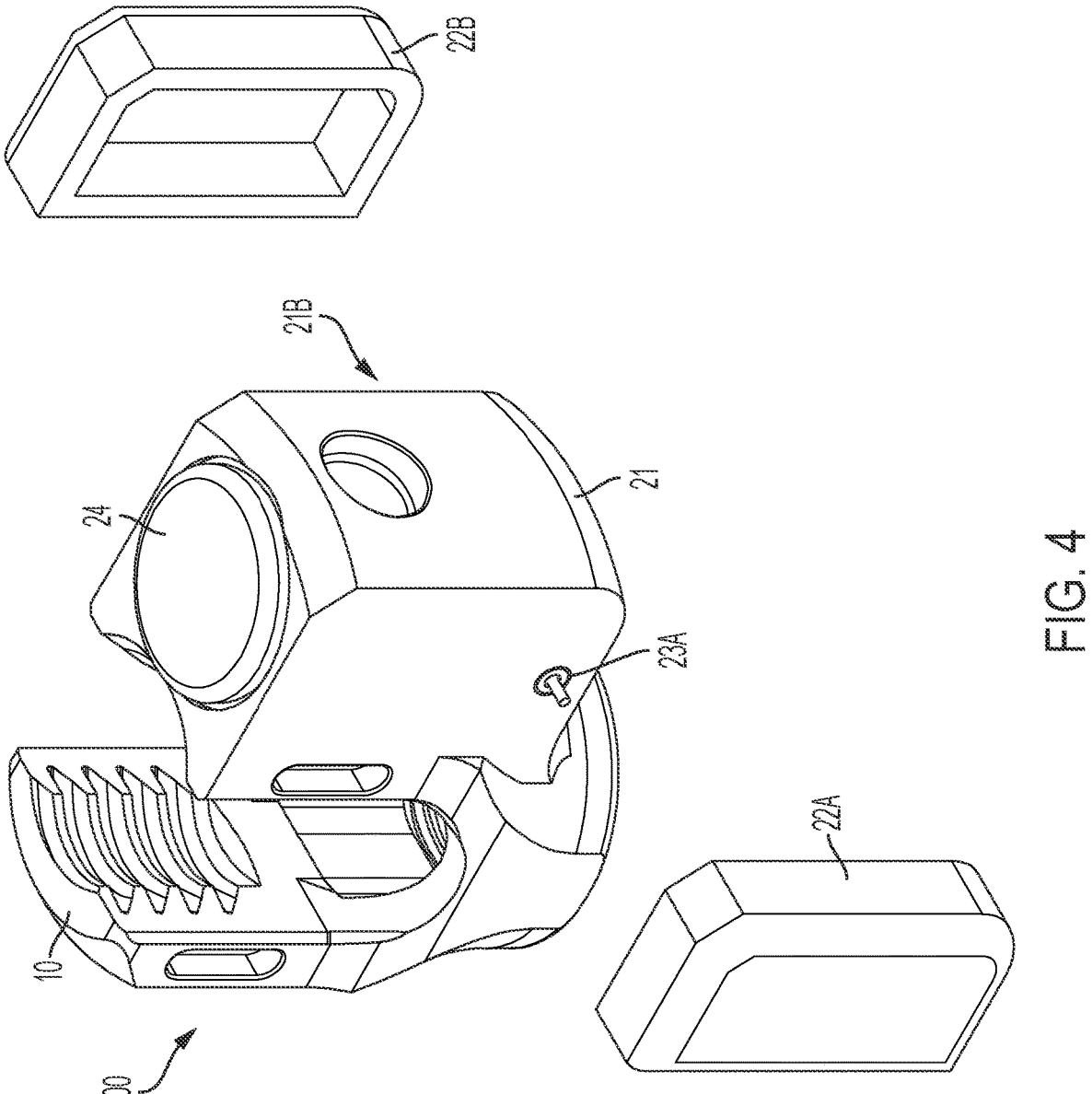
FIG. 4 shows an exploded view of another example smart implant.

In some embodiments, the antenna portion 22 may be included within or closely adjacent to the cavity. For example, FIG. 4 shows an exploded view of another example compact smart implant 110. In the example embodiment, the microelectronics assembly 30 and battery 31 may be disposed inside of the cavity 25 and the cavity 25 may be sealed off by cover 24. In this embodiment, cover 24 is a circular plate that is dimensioned to cover a corresponding opening in the top portion of housing 21. Additionally, in this embodiment, a first antenna portion 22A is disposed on a first sidewall 21A of housing 21 and a second antenna portion 22B is disposed on a second sidewall 21B of housing 21. For example, the first antenna portion 22A is disposed on an opposite sidewall of the housing 21 opposite the second antenna portion 22B. In this embodiment, the antenna portions 22A and 22B include a corresponding cavity for housing any suitable type of antenna, e.g., a grid antenna or a patch antenna and/or any combination of antennas as explained previously. In some embodiments, each cavity of the antenna portions 22A, 22B may house different types of antenna having different communication frequencies and protocols.

A first feed-through connection 23A having suitable waterproof flanges may extend through first sidewall 21A and a second feed-through connection 23B (not shown) having suitable waterproof flanges may extend through second sidewall 21B. In this way, the feed-through connections 23A and 23B may be electrically connected to the microelectronics assembly 30 and the antenna portions 22A, 22B while ensuring that a hermetic seal of the electronics components is possible.

Various antenna and communication types may be, for example, MICS and BLE. As used herein, "MICS" may refer to the Medical Implant Communication System which may be a short-range communication technology that operates at a frequency from about 402 to 405 MHz. As used herein, "BLE" may refer to Bluetooth low energy communication standard. In some embodiments, the antenna may be a multi-band electrically coupled loop antenna (ECLA) antenna capable of operating in at least the MICS and LBE bands.

Referring back to FIG. 1, in some examples, one or more smart implants 110 are configured to sense forces or strains that are applied by (or experienced by) one or more components of the construct 102 during the procedure. Force sensors include strain gauges, load cells, piezoelectric sensors, or other similar devices that sense force or strain. Force sensors may be configured to sense a force applied directly to the sensor by a component of the construct. Force sensors may also be configured to sense a degree of deformation of a component of the construct. For example, a strain gauge may measure the amount that a spinal rod is bent by forces applied to the rod. The bending force may be applied to the rod at points that are spaced at a distance from the sensor. The measured deformation of the rod may be converted to a level of force applied to the rod based on the characteristics and configuration of the rod. In some examples, at least one smart implant 110 is configured to attach to multiple components of the construct 102, or to attach to a component and a part of the patient's anatomy, such that the smart implant 110 can sense a force between the components and/or the patient's anatomy. Providing intra-operative telemetry related to forces associated with the construct 102 allows for intra-operative adjustments to the construct 102 during assembly/installation. Adjustments may include, e.g., (a) bending and/or contouring a spinal rod, e.g., to increase or decrease force applied to the implants or the patient's spine, (b) attaching the construct to the patient's spine at additional points so that forces are dissipated, rather than concentrated at any single fixation point, and/or (c) adding one or more cross links between spinal rods (or other components) in order to decrease rotational forces, etc. In some examples, after the construct 102 has been configured, some or all of the smart implants 110 may be removed.

In some examples, one or more smart implants 110 are configured to attach to a part of the patient's anatomy, e.g., to sense forces and provide telemetry during the procedure. Telemetry data may include position/motion information, force/strain information, temperature, tissue impedance, and so forth. For example, the smart implant 110 may be configured to attach to a vertebra of the patient, e.g., using a screw, hook, tether, or other means. In some examples, the smart implant 110 is configured to temporarily attach to the part of the patient's anatomy. That is, the smart implant 110 may be detached from the patient's anatomy and/or removed after the construct 102 has been configured. For example, as disclosed above, the smart implant 110 may attach to a vertebra using a bone screw, such as pedicle screw 2, which may be easily de-coupled from the remainder of the smart implant 110. In that way, the smart implant 110 may provide telemetry related to sensed forces between the vertebra and the construct (e.g., the rod 106 that the smart implant 110 is attached to) during the procedure. After the construct 102 has been configured, the smart implant 110 may be decoupled from the pedicle screw 2 and may be removed. In other examples, the smart implant 110 temporarily attaches to the patient's anatomy using a hook, tether, or other means which may be disconnected after the construct 102 is configured.

Figure 5:
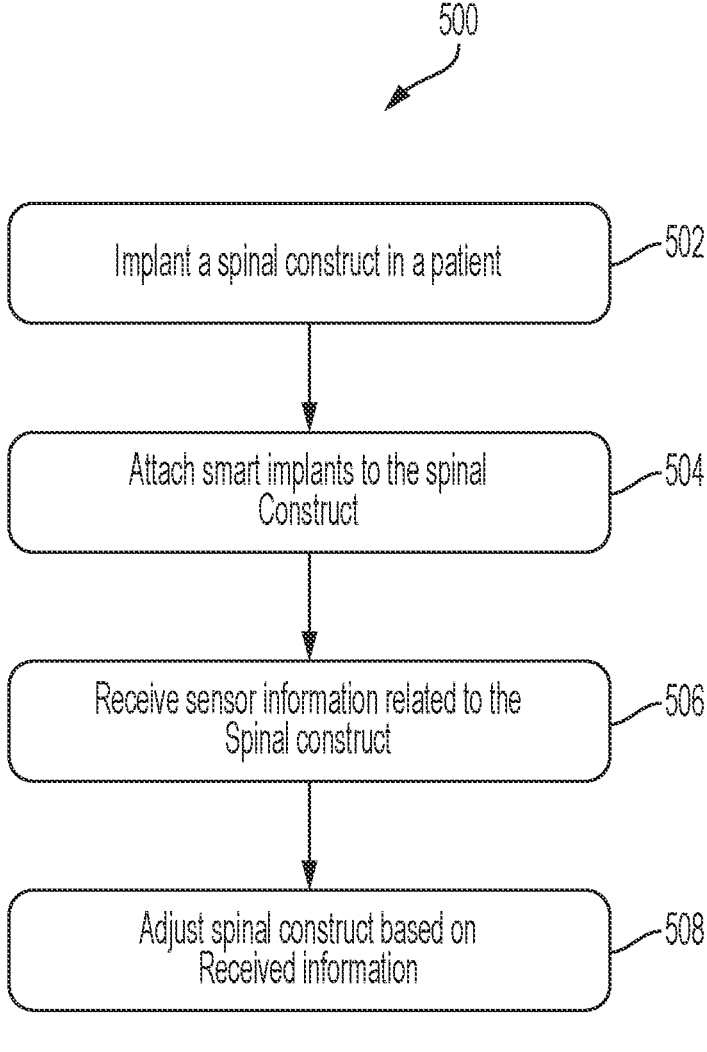
FIG. 5 shows a flowchart for an example method.

FIG. 5 illustrates a flowchart 500 of an example method of treating a spine including interoperative use of smart implant 110. At step 502, the method includes implanting at least a portion of a spinal construct 102 in a patient. As disclosed above, the spinal construct 102 may include components such as bone screws (e.g., pedicle screws), transverse process hooks, rods, cross connectors, accessories, and so forth. At step 502, some or all of the components are attached to a part of the patient's anatomy, such as a vertebra. Other components may be included as well, and may be attached to, e.g., another part of the patient's anatomy, or attached to other components of the construct 102.

At step 504, the method includes attaching one or more smart implants 110 to the spinal construct 102. Each smart implants 110 includes an attachment portion configured to attach the smart implant to the spinal construct 102 and at least one sensor configured to measure an aspect of the spinal construct 102. In some examples, the sensor is configured to measure a force between the spinal construct 102 and a bone, such as a vertebra. In some examples, the sensor is configured to measure strain applied to one or more components of the construct. In some examples, the sensor is configured to measure position, motion, or temperature related to the spinal construct 102.

As disclosed above, the smart implant 110 may be temporarily attached to the patient's anatomy in order to provide intra-operative telemetry related to the construct 102. After the construct 102 is configured, the smart implant 110 may be disconnected (and possibly removed). Furthermore, the construct 102 itself may include temporary or provisional components that are installed during the procedure, in order to provide intra-operative telemetry related to the construct 102, and may be removed after the construct 102 is configured. For example, the construct 102 may include a provisional spinal rod having the primary purpose of supporting intra-operative telemetry.

The provisional spinal rod may be rigidly attached to another, e.g., permanent, component of the spinal construct 102, and one or more smart implants 110 may be attached to the provisional spinal rod. In this way, the smart implants 110 that are attached to the provisional spinal rod may be able to measure aspects of the construct 102 in an independent way or measure aspects that cannot otherwise be measured. In an example, one or more smart implants 110 attached to the provisional spinal rod may also be attached to the patient's anatomy, such that the smart implants 110 may provide telemetry related to the distribution of forces applied by the spinal construct 102 to the patient's anatomy. In some examples, the temporary placement of the provisional spinal rod allows the smart implants 110 to measure forces applied to vertebrae from different angles or orientations than would be achievable from permanent components of the spinal construct 102. After the construct 102 is configured, the temporary or provisional components may be removed, the temporary spinal implants 110 may be decoupled from the patient's anatomy, and the temporary spinal implants 110 may also be removed.

At step 506, the method includes receiving sensor information related to the measured aspect of the spinal construct 102 from the one or more smart implants 110. In some examples, the information is received by an external receiver device, i.e., a reader device outside of the patient's body. For example, a reader device may be configured to wirelessly receive information transmitted from the one or more smart implants 110. The reader device may include a display screen and may display the received information or otherwise make the information available to the surgeon who is installing and configuring the construct 102. In some examples, the reader device displays a plot of the information received, e.g., to show relative changes to the measured aspect over time, e.g., as the surgeon further configures the construct.

Alternatively (or additionally), one or more tools or instruments may include a reader which may be used to gather information from one or more integrated circuits of electronic components 30 during or in connection with a procedure. For instance, a torque tool (not illustrated) may be used to loosen or tighten a set screw 4 connecting the smart implant 110 to a longitudinal rod 106. A torque tool may include a reader, or may be in communication with a reader, such that a user of the torque tool is able to obtain, in substantially real time, one or more measurements relating to the smart implant 110 and longitudinal rod 106 placement that are measured by a strain gauge 32 of a load sensing assembly of the smart implant 110 via the tool. For instance, as a user is applying torque to a set screw 4, the user may see one or more force measurements between the smart implant 110 and the longitudinal member 106 in order to determine that the positioning of the smart implant 110 and/or longitudinal member 106 is correct and that the proper force is being maintained. In certain embodiments, a tool or instrument may include a display device (not illustrated) on which one or more measurements may be displayed. In other embodiments, a tool or instrument may be in communication with a display device (not illustrated), and may transmit one or more measurements for display on the display device via a communications network.

In some embodiments, an electronic device, such as a reader or an electronic device in communication with a reader (not illustrated), may compare one or more measurements obtained from an integrated circuit to one or more acceptable value ranges. If one or more of the measurements are outside of an applicable value range, the electronic device may cause a notification to be made.

The received data may indicate, for example, whether forces are appropriately distributed throughout the construct 102. In some examples, smart sensors 110 may be installed throughout the construct 102 to provide, with high spatial resolution, information related to the distribution of forces. The received information may disclose issues with the integrity of the construct 102, such as a component which is not properly fastened. The received information may disclose which spinal levels should be included in the construct 102. For example, the intra-operative information may disclose larger than expected forces being applied to the upper instrumented vertebra (UIV), suggesting that the construct 102 should be extended to include an additional spinal level to reduce the chance of PJK.

At step 508, the method includes performing at least one intra-operational adjustment to the spinal construct 102 based on the received sensor information. As disclosed above, the adjustment may be related to redistributing forces, e.g., by reconfiguring the construct 102. Reconfiguring the construct 102 may include repositioning components, replacing components, adding or removing components, and so forth. In some examples, the adjustment includes extending the construct 102 to include additional spinal levels. The adjustment may also include reducing the total number of spinal levels involved.

In some examples, the method further includes repeating any or all of steps 504-508 until the surgeon is satisfied with the configuration and integrity of the construct 102 and the distribution of forces throughout the construct 102. In some examples, after the surgeon is satisfied that no further adjustments are needed, the method further includes removing one or more of the smart implants 110.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

The breadth and scope of this disclosure should not be limited by any of the above-described example embodiments, but should be defined only in accordance with the following claims and their equivalents.

What is claimed is:

1. A method of treating a spine, the method comprising:
   implanting at least a portion of a spinal construct in a patient;
   attaching one or more smart implants to the spinal construct, each of the one or more smart implants comprising:
   an attachment portion configured to attach the smart implant to the spinal construct; and
   at least one sensor configured to measure an aspect of the spinal construct during a time that the smart implant is attached to the spinal construct, wherein the aspect comprises a force applied to one or more components of the spinal construct, and wherein the smart implant is configured to transmit information related to the measured force;
   receiving, from the one or more smart implants, the transmitted sensor information related to the aspect of the spinal construct;
   performing at least one intra-operational adjustment to the spinal construct based on the received sensor information by reconfiguring the construct to redistribute the forces applied to the one or more components of the spinal construct as measured by the one or more smart implants; and
   removing at least one of the one or more smart implants after performing the at least one intra-operational adjustment to the spinal construct without replacing the at least one of the one or more smart implants.

2. The method of claim 1, wherein performing the at least one intra-operational adjustment to the spinal construct comprises: bending a spinal rod of the spinal construct, adding a cross link to the spinal construct, or affixing the spinal construct to the patient at one or more additional points.

3. The method of claim 1, wherein the one or more smart implants comprises a plurality of smart implants.

4. The method of claim 1, wherein:
at least one smart implant comprises a force sensor;
receiving the sensor information related to the aspect of the spinal construct comprises receiving information from the force sensor; and
performing the at least one intra-operational adjustment to the spinal construct comprises performing the at least one intra-operational adjustment based on the received information from the force sensor.

5. The method of claim 4, wherein receiving the information from the force sensor comprises receiving strain data from the force sensor.

6. The method of claim 1, wherein:
at least one smart implant comprises a position sensor; and
receiving the sensor information related to the aspect of the spinal construct comprises receiving information related to a position of the smart implant when the smart implant is attached to the spinal construct.

7. The method of claim 1, wherein:
at least one smart implant comprises an antenna; and
receiving the sensor information related to the aspect of the spinal construct comprises receiving the sensor information wirelessly.

8. The method of claim 1, wherein performing the at least one intra-operational adjustment to the spinal construct comprises implanting additional construct components.

9. The method of claim 1, wherein attaching the one or more smart implants to the spinal construct comprises:
adding a provisional component to the spinal construct; and
attaching at least one of the one or more smart implants to the provisional component.

10. The method of claim 9, further comprising attaching the at least one of the one or more smart implants to a part of the patient's anatomy.

11. The method of claim 9, further comprising, after performing the at least one intra-operational adjustment to the spinal construct, removing the provisional component.

12. The method of claim 1, wherein:
the spinal construct comprises a spinal rod; and
attaching the one or more smart implants to the spinal construct comprises securing the spinal rod within an opening of at least one of the one or more smart implants.

13. The method of claim 1, further comprising attaching at least one of the one or more smart implants to a part of the patient's anatomy.

14. The method of claim 13, wherein:
the at least one of the one or more smart implants comprises a bone screw; and
attaching the at least one of the one or more smart implants to the part of the patient's anatomy comprises attaching the at least one of the one or more smart implants to a bone using the bone screw.

15. The method of claim 13, further comprising, after performing the at least one intra-operational adjustment to the spinal construct, detaching the at least one of the one or more smart implants from the part of the patient's anatomy without reattaching the at least one of the one or more smart implants.

16. The method of claim 1, wherein receiving the sensor information related to the aspect of the spinal construct comprises receiving the sensor information by an external reader device.

17. The method of claim 16, wherein receiving the sensor information related to the aspect of the spinal construct comprises viewing a plot of the sensor information displayed by the external reader device.

18. The method of claim 16, wherein receiving the sensor information related to the aspect of the spinal construct comprises receiving a notification, from the external reader device, that one or more sensor measurements are outside of a value range.

19. The method of claim 1, wherein performing the at least one intra-operational adjustment to the spinal construct comprises extending the construct to include additional spinal levels.

20. The method of claim 1, wherein reconfiguring the construct to redistribute the forces applied to the one or more components of the spinal construct comprises bending and/or contouring a spinal rod to increase or decrease a force measured by at least one of the one or more smart implants.

21. A method of treating a spine, the method comprising:
implanting at least a portion of a spinal construct in a patient;
attaching one or more smart implants to the spinal construct, each of the one or more smart implants comprising:
an attachment portion configured to attach the smart implant to the spinal construct; and
at least one sensor configured to measure an aspect of the spinal construct during a time that the smart implant is attached to the spinal construct, wherein the aspect comprises a force applied to one or more components of the spinal construct, and wherein the smart implant is configured to transmit information related to the measured force;
attaching at least one of the one or more smart implants to a part of the patient's anatomy;
receiving, from the one or more smart implants, the transmitted sensor information related to the aspect of the spinal construct;
performing at least one intra-operational adjustment to the spinal construct based on the received sensor information by reconfiguring the construct to redistribute the forces applied to the one or more components of the spinal construct as measured by the one or more smart implants; and
after performing the at least one intra-operational adjustment to the spinal construct, detaching the at least one of the one or more smart implants from the part of the patient's anatomy without reattaching the at least one of the one or more smart implants.

* * * * *